Figure 1:
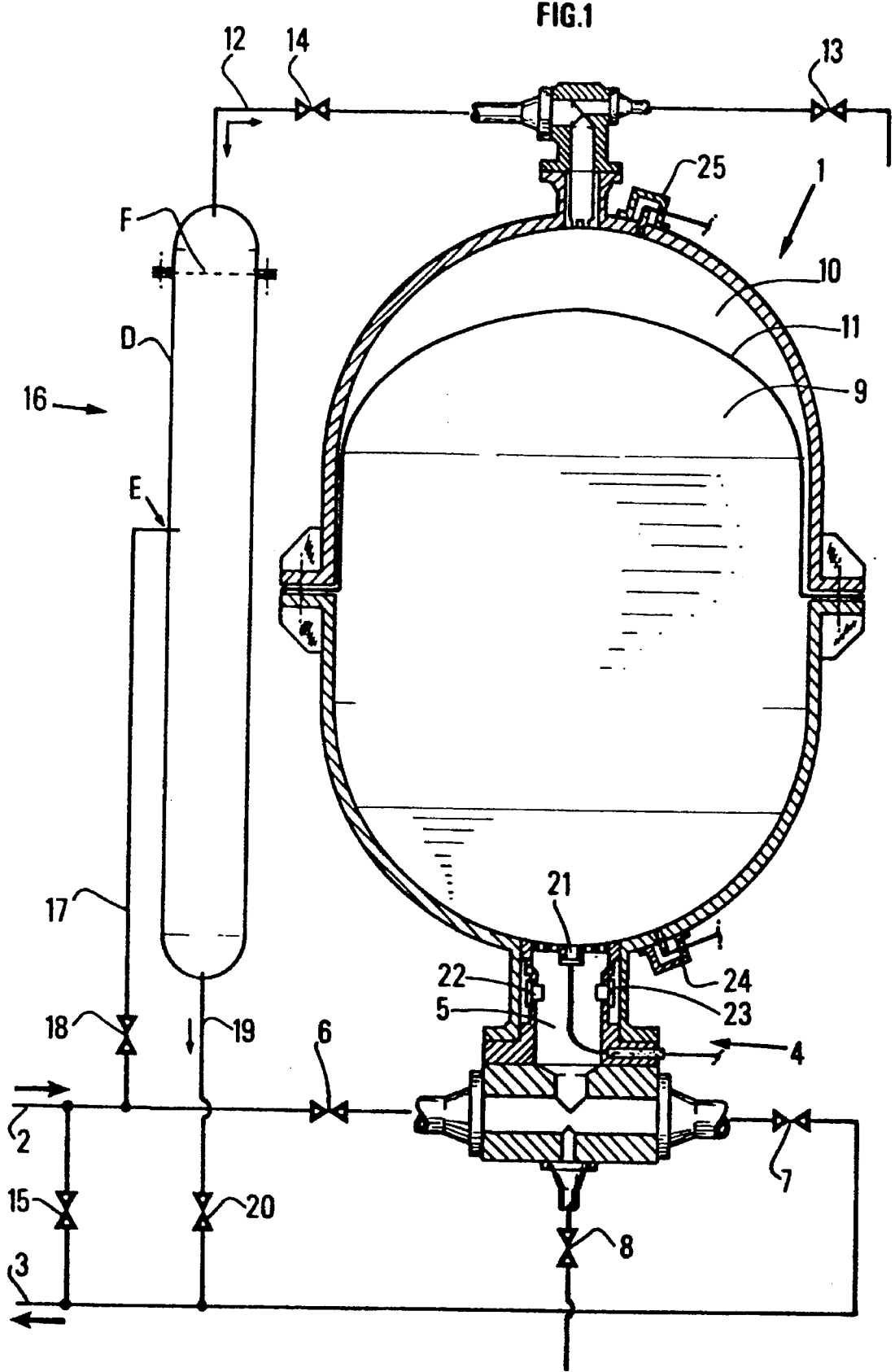

United States Patent [19]

Castel

[11] Patent Number: 5,616,856
[45] Date of Patent: Apr. 1, 1997

[54] DEVICE AND METHOD FOR DETECTING INTERFACES SEPARATING SEVERAL PHASES BY ULTRASONIC WAVES

[75] Inventor: Yvon Castel, Croissy sur Seine, France

[73] Assignee: Institut Francais du Petrole, Rueil Malmaison, France

[21] Appl. No.: 364,936

[22] Filed: Dec. 28, 1994

[30] Foreign Application Priority Data

Dec. 28, 1993 [FR] France .................. 93 15856

[51] Int. Cl.⁶ .................................. G01N 3/22
[52] U.S. Cl. ........................ 73/61.45; 73/61.44
[58] Field of Search .................. 73/61.43, 61.44, 73/61.45, 61.49, 290 V, 1 H

[56] References Cited

U.S. PATENT DOCUMENTS

| | | | |
|---|---|---|---|
| 4,414,849 | 11/1983 | Brown et al. | 73/290 V |
| 4,427,132 | 1/1984 | Thomson | 73/290 V X |
| 4,565,088 | 1/1986 | Crambes | 73/61.49 |
| 4,852,396 | 8/1989 | Tavlarides et al. | 73/61.45 |
| 4,918,979 | 4/1990 | Pearce et al. | 73/61.44 X |
| 5,033,288 | 7/1991 | Castel | 73/61.44 |
| 5,043,912 | 8/1991 | Reus | 73/290 V X |
| 5,060,507 | 10/1991 | Urmson et al. | 73/61.49 X |
| 5,473,934 | 12/1995 | Cobb | 73/61.49 |

FOREIGN PATENT DOCUMENTS

| | | |
|---|---|---|
| 0087365 | 8/1983 | European Pat. Off. . |
| 0115987 | 8/1984 | European Pat. Off. . |
| 0384373 | 8/1990 | European Pat. Off. . |
| 3431741 | 3/1986 | Germany . |

OTHER PUBLICATIONS

Advances in Instrumentation and Control, vol. 46, No. 2, 1991, NC, USA, pp. 1355–1366; XP347570 D. Duncan, "Ultrasonics in Solids Level Measurement".

*Primary Examiner*—Elizabeth L. Dougherty
*Attorney, Agent, or Firm*—Antonelli, Terry, Stout & Kraus, LLP

[57] ABSTRACT

The presence of interfaces located between at least two phases having close but different acoustic impedance values and two phases having relatively remote acoustic impedance values is detected, at least one of these phases being likely to contain solid particles. A device for detecting the presence of the interfaces includes a container linked to at least one intake pipe for a multiphase fluid, a first unit for generating an ultrasonic wave in a direction not parallel to an interface, this unit also being designed to receive a signal generated by a reflection of the wave on the interface, and a processing unit which enables various measurements to be taken and processed so as to calculate the quantity of at least one of the phases present in a multiphase fluid.

10 Claims, 3 Drawing Sheets

DEVICE AND METHOD FOR DETECTING INTERFACES SEPARATING SEVERAL PHASES BY ULTRASONIC WAVES

The present invention relates to a method and a device for detecting by means of ultrasonic waves interfaces separating phases having different acoustic impedances.

It is especially well suited to detecting interfaces located between the phases that make up a fluid, particularly for detecting the interface located between an aqueous phase and an organic phase and the interface situated between an organic phase and a gaseous phase, one of these phases possibly comprising solid materials, such as sand.

It is therefore used in applications involving a petroleum fluid or effluent made up of water, oil and gas, particularly containing hydrocarbon.

For the specific reasons outlined below, a device and method are needed during petroleum production that will enable, either on a continuous basis or by successive sampling, the quantity of each of the phases making up the petroleum effluent to be determined, these phases being measured as they are brought out from the production well. With this information, the producer is able to ascertain the real volume of each phase of the effluents drawn off from a deposit during production and can thus deduce the exact price he will have to pay, determine the efficiency of any stimulation processes that might be used, regulate production of the wells to obtain maximum profitability from the deposit and settle the taxes, particularly on fixed price products.

Another example of an application is in the instance when multiphase petroleum effluents are transported without separating the phases and in the use of pumping devices where optimum operation at any one time is dependent on the composition of the effluents and more especially on knowing the mean liquid flow rate and the volumetric gas/liquid ratio.

Various methods and devices are currently used to determine the composition of a multiphase effluent.

French patent FR-2.633.719 by the applicant describes a sampling device in which a container is fitted with a mobile arm inside the container, the arm supports one or several sensors and the arm and sensor assembly configured in this manner is used to locate the position of the interfaces between the different phases making up the fluid once it has been decanted into the container. From the position of the interfaces and the geometry of the container, it is possible to work out the quantity of each of the phases contained in the container. However, being a mechanical device, the arm is intrusive and because of its displacement it disturbs the equilibrium of the existing interfaces. Furthermore, it has been discovered that an adhesive film could form on the sensors, leading to errors and/or uncertainty in the measurements.

Patents FR-2.522.153 and U.S. Pat. No. 5,119,676 describe the use of ultrasonic waves to determine the quantity of an aqueous phase and a gaseous phase. In the first document, the quantity of water and the quantity of water vapour, whether dissolved in the form of bubbles or not dissolved in the water, is measured by combining the propagation time values of the ultrasonic waves obtained for two frequency values and the values of the propagation speeds of these waves in the water and the gas. On the basis of the description contained in this document, it is, therefore, possible to work back to the quantity of two water and water vapour phases whose acoustic characteristics are very different.

The second document describes the positioning of the ultrasonic sensor outside a container so as to remove it from the temperature and pressure conditions prevailing inside the container that might prove to be a constraint. It also describes the operation of a focused beam of ultrasonic waves, which is guided in a tube in order to eliminate reflections caused by interference that might lead to errors in the measurements. In this patent, an interface located between two media whose values of acoustic impedances are relatively remote is detected.

These two documents relate solely to detecting a wave reflected almost in its entirety on a single interface located between two phases whose impedance values are remote.

The use of ultrasonic waves is known in the field of petroleum exploration as a means of controlling the level of interfaces separating two phases of an effluent in a container. The equipment marketed by the company, Milltronics, comprises ultrasonic sensors positioned in the upper part of the container on the side of the gaseous phase of the effluent. This position is dictated by the need for easy access and by the fact that solid material such as solid particles of sand, hydrates . . . might be present in the effluent. The accumulation of these particles under the effect of gravity can obstruct any sensor located in the lower section of the container.

It has been discovered, and this is the objective of the present invention, that it is possible to determine the presence of interfaces located between two phases having close but different values of acoustic impedance and two interfaces having relatively remote values of acoustic impedance, where at least one of the phases is likely to contain solid particles, without encountering any of the disadvantages mentioned above. The result is obtained by using a non-intrusive measuring device that makes it possible to detect the echoes of waves reflected on the interfaces and measure the propagation time of these reflected waves. This device is completed by a filtering means, for example, for any solid particles that might be contained in the effluent.

Throughout the following description, the terms "phase" and "fluid medium" are used to denote the same element, particularly the different parts of the medium having different acoustic values, these different parts taken as a whole forming the fluid medium analyzed.

The present application relates to a device for determining the composition of a multiphase fluid made up of several phases, these phases being separated by an interface, at least two of these phases having acoustic impedances of values that are essentially remote and at least two of these phases having acoustic impedance values that are substantially close but different, the fluid possibly containing solid particles, comprising a container linked to at least one intake pipe for the multiphase fluid, at least a first means located in the container to generate a first ultrasonic wave in one direction, not parallel to the interface separating at least two phases, this first means being designed to receive at least one signal from the reflection of the first ultrasonic wave when it encounters an interface separating two phases, second means for emitting and receiving a second ultrasonic wave and processing means. It is characterised in that the second means are arranged so as to emit and receive the second ultrasonic wave in a direction that is substantially perpendicular to the direction in which the first ultrasonic wave was propagated and in that the processing means enables the propagation time of the first wave to an interface to be measured as well as the propagation time of the second wave through a phase and, on the basis of data previously stored in the memory of the processing means and the various propagation time measurements, the quantity of at least one of the phases contained in this multiphase fluid to be determined.

The first ultrasonic wave is transmitted in a direction that is, for example, substantially perpendicular to the interface and the ultrasonic wave meets this interface.

The device may have a system for filtering any solid particles contained in the fluid, one of the specific aims of the system being to avoid any build-up of particles in the lower section of the container.

It may also incorporate means for controlling and regulating a means for filling and emptying the container.

The present application also relates to a method for determining by means of at least one ultrasonic wave the composition of a multiphase fluid having several phases, where at least two of these phases have acoustic impedances of different values, the fluid possibly containing solid particles. It is characterised in that:

a) at least a proportion of the multiphase fluid is drawn off into the container for analysis, b) the multiphase fluid is left to decant for a sufficient period of time to allow the different phases to separate, c) a first ultrasonic wave is transmitted in a direction that is not parallel to a first interface separating two phases and the wave is propagated and passes through the container, d) using an appropriate device, at least a first propagation time T1, representing the reflection of this first ultrasonic wave on a first interface, is measured, e) a second ultrasonic wave is transmitted, in a direction substantially perpendicular to the direction in which the first wave was propagated, through a first phase, when this first phase is in the lower part of the container and the propagation time T1 of the second wave in this first phase is measured so that the real propagation speed V1 of the wave in the first phase can be calculated from it and f) using the first propagation time T1, the real speed value V1 and the geometric characteristics of the container, the quantity U1 of the first phase in the container is determined.

The multiphase fluid may comprise several phases, at least a first and a second phase having acoustic impedances of essentially remote values and at least a second phase and a third phase having acoustic impedance values sufficiently close but different and possibly having solid particles. The procedure would then be as follows:

steps a) to e) described above are carried out, at least the propagation times T1 and T2 are measured, representing respectively the reflection of this first ultrasonic wave on the first and second interfaces separating respectively the first and second phases and the second and third phases, the real propagation speed of the wave in the first phase is measured in accordance with step e) described above, the fluid is drained from the container over a sufficient period of time to allow the second phase to reach the level of the lower part of the container and a second ultrasonic wave is emitted in a direction substantially perpendicular to the propagation direction of the first wave through a first phase, this phase being located in the lower part of the container, and the propagation time T2 of the second wave in the second phase is measured in order to ascertain the real propagation speed V2 of the wave in the second phase, and using the propagation times T1 and T2, the real speed values V1 and V2 and the geometric characteristics of the container, the quantities U1 and U2 of the first and second phases are determined.

The attenuation of the wave after reflection on an interface may be measured.

The method also makes it possible to avoid a build-up of deposits of solid particles in the container, fitted with a membrane, by proceeding with the following steps:

at least a proportion of the multiphase fluid which will be the analysis sample is drawn off into the container, the proportion of fluid drawn off is left to decant and measurements are then taken, once the measurements have been completed, a quantity of fluid which has previously been passed through a filtering device is introduced via the upper part of the container, this quantity of fluid being sufficient to push the membrane towards the lower part of the container so as to discharge the sample of multiphase fluid, and any particles that have formed a sediment in the lower part of the container are then carried along with the sample discharged from the container.

In the case of a multiphase fluid comprising at least three phases, the quantity of the third phase may be determined by using, for example, the geometric characteristics of the container and the quantities U1 and U2.

In addition, the time t needed to fill the container completely can be measured and this time t may be used to calculate the flow rate of each of the phases making up this fluid.

Whilst the container is being filled, it is possible to check whether the multiphase fluid taken as a sample is representative.

One of the possible applications of the method and device of the invention is in determining the composition of a petroleum effluent.

The method and device of the invention may also be used in applications for detecting a first interface located between an aqueous phase and an organic phase and a second interface separating an organic phase and a gaseous phase, these phases making up the greater part of the petroleum effluent.

The method and device of the invention may also be applied when determining the flow rate of each of the phases contained in a petroleum effluent.

Figure 2:
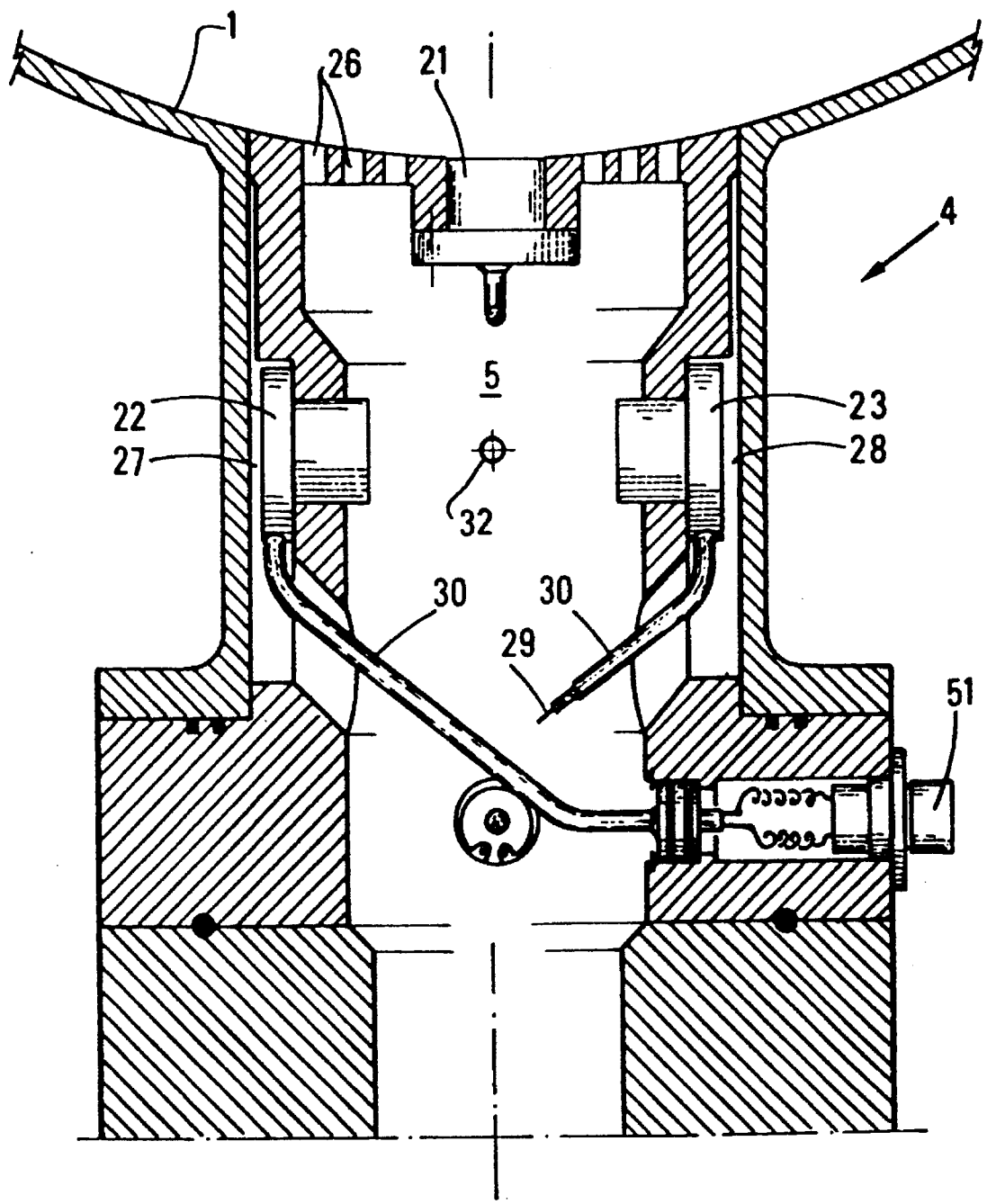
Figure 3:
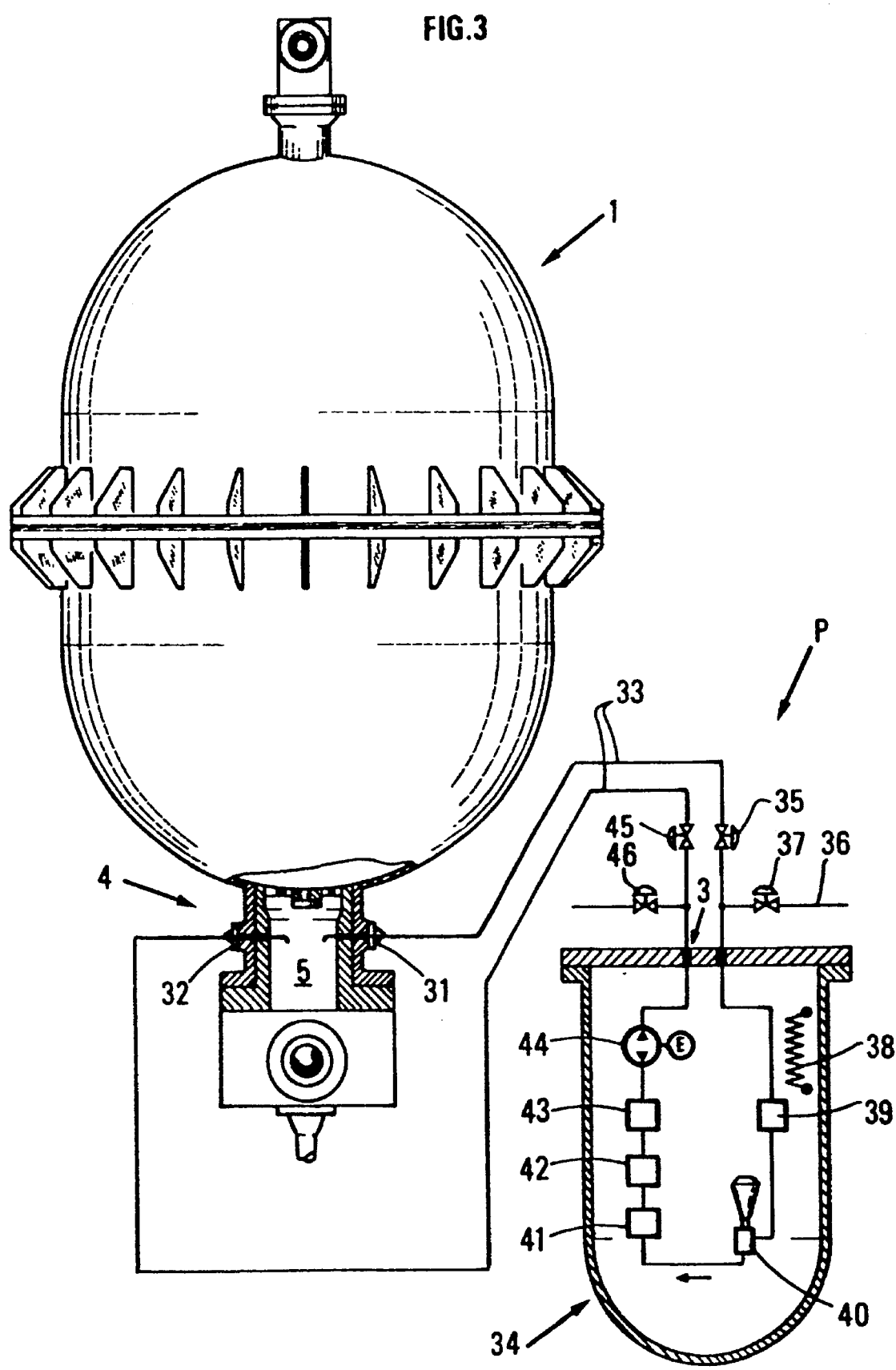

The present invention will be more readily understood and its advantages more clearly seen from the description of several embodiments illustrated by the attached drawings, in which:

FIG. 1 is a schematic illustration of a device of the invention applied to the process of determining the quantity of each of the phases contained in a multiphase effluent, FIG. 2 shows in more detail the lower section of the device, equipped with ultrasonic wave transmitters-receivers, and FIG. 3 shows a device in which the container is connected to a series of analyzers.

The underlying principle of the invention described below is the fact that the reflection of an ultrasonic wave being propagated in a medium having several phases of different acoustic impedances is dependent on the difference in acoustic impedance values separating two adjacent successive phases. As a result, when two phases have acoustic impedance values that are relatively remote, the wave reflects almost in its entirety on the interface separating these two phases, whereas if two phases have impedance values that are essentially close but different, the ultrasonic wave is reflected only partially on the interface. The signals from the reflections therefore have different characteristics.

Interfaces can be detected without any disturbance that might be caused by the presence of an intrusive measuring instrument.

By combining the results of measurements of ultrasonic wave echoes on an obstacle and the propagation time of the wave in different fluid media or phases, it is possible to ascertain the quantity of each of the phases making up a multiphase fluid.

At the same time, measurements of the forward and throwback time of an ultrasonic wave, more commonly known as the flight time, may be measured as a means of determining the real propagation speed of a wave in a phase and thus overcome the effect of parameters such as the temperature or nature of the phases.

The device and method of the invention function best at the values of acoustic impedance ratios given below:

in instances where the acoustic impedance values are substantially close, the interval of variation in the acoustic impedance ratio separating two phases varies, for example, between 0.5 and 10 and, where these acoustic impedance values are remote, a ratio value varying, for example, in a range from 1,000 to 5,000.

These values are given solely as an indication and are not limitative, and relate more specifically to the application described below.

Apart from measuring the arrival or reception of waves reflected on the interfaces, the signals reflected by the interfaces may be analyzed in terms of amplitude and frequency shift, by means of the procedures conventionally used to analyze signals. This analysis makes it possible, for example, to follow changes in the qualities of the effluent collected in the container over a period of time, in which case the analyzed signals are correlated, for example, with the results previously obtained from the reference samples.

At the same time, the method also makes use, for example, of a filtering system or device for draining the fluid sample contained in the container to carry away any particles that have deposited and built up in the lower part of the container and that might obstruct the ultrasonic wave device.

The device of FIG. 1 is particularly well suited to analysing and quantifying the phases contained in a multiphase petroleum effluent, i.e. an aqueous phase such as water, an organic phase such as oil and a hydrocarbon gas phase. The different phases are usually accompanied by solid particles, such as sand or hydrates which may, under the effect of their weight, fall and accumulate on the ultrasonic transmitter-receiver leading to inaccurate measurement values. In the embodiment given as an example here, the effluent is drawn off via a transfer pipe to a tank or container 1 in which it is decanted to allow the phases to separate naturally.

The tank 1 is connected, via a base 4 to an intake pipe 2 and a discharge pipe 3 for the effluent. The pipes 2 and 3 are, for example, by-pass pipes connected to a main pipe transferring effluent between a source and a processing point, not shown in the drawing for reasons of simplification. The pipes 2 and 3 extend into the base 4 by means of a pipe 5 opening into the tank 1.

The pipes 2 and 3 are fitted respectively with an inlet valve 6 controlling the input of effluent and a discharge or outlet valve 7 for the effluent.

The pipes 2 and 3 are connected to each other by a pipe fitted with a by-pass 15.

In its lower section, the base 4 has a pipe 8 for draining the tank.

The tank 1 comprises an intake chamber 9 and an auxiliary chamber 10 separated from each other by a flexible membrane 11. The effluent drawn in is stored until the intake chamber 9 is completely full and, once the different constituent phases have naturally separated, analyzed using at least one ultrasonic wave in accordance with the steps described below, for example.

The auxiliary chamber 10 is connected on the one hand to a compensation pipe 12 fitted with an isolation valve 14 and on the other hand by a drain valve 13 preferably located at the head of the auxiliary chamber 10.

The compensation pipe 12 links the intake chamber 9 to a filtering device 16 comprising, for example, a decanting flask D fitted with a filter F located in its upper part, the chief role of which is to prevent the entry of any solid particles, sand or hydrates for example, into the tank 1, when the contents of the tank of chamber 9 are being drained.

The device 16 is also connected to the effluent inlet pipe 2 by a pipe 17 having a by-pass valve 18, this pipe opening into the decanting flask D via an off-centre lateral inlet E which induces a cyclone effect to encourage separation of the solid particles from the effluent. It is connected to a pipe 3 which returns the effluent by means of a pipe 19 fitted with a valve 20, this pipe being located in the lower part of the flask D so as to discharge the solid particles moving downwards under the effect of gravity.

The position of the filter F in the lower part of the flask D is selected so that the speed of the effluents is reduced as the effluent passes through it.

For instance with a flask D of a diameter of 20 mm, the inlet would have a diameter of 4 mm, for example. The filter F may be a 10 m filter, thus providing a passage rate of about 10%.

The filtering device 16, the tank 1 and the pipes 2 and 3 are configured in such a way that they form a self-cleaning system. In effect, when the lower part of the tank 1 is drained, the effluent that is expelled cleans the filter by carrying the particles deposited on its lower surface to the lower part of the decanting flask D and through the pipe 19.

The lower part of the tank 1 is fitted with means designed to measure the flight time of an ultrasonic wave. It therefore comprises in its lower part a transducer or transmitter-receiver 21 emitting an ultrasonic wave in the direction of at least one of the interfaces separating the different phases of the effluent. It also has an assembly made up of a transmitter 22 and a receiver 23 generating and receiving ultrasonic waves through the effluent flowing in the pipe 5. The transmitter 22 and the receiver 23 are in a different shift from each other so as to take a flight time measurement in a manner known to specialists and thus measure the real propagation speed of the ultrasonic wave in each of the phases making up the effluent. Measurement by this method is advantageous since it improves the calculation of the phase quantities by replacing the estimated propagation speed of the wave in a phase with an actual measurement, as shown subsequently in this description.

The devices 21, 22 and 23 and their configuration are therefore described in greater detail with reference to FIG. 2.

Position sensors 24 and 25, arranged respectively in the lower and upper part of the container make it possible to control the filling of the tank by controlling, for example, the position of the membrane 11.

The device also has a means for controlling the different steps used in accordance with the method described below, such as a micro-controller M, not shown in FIG. 1. This processor is fitted, for example, with a signal acquisition and generation card and a processing and driving logic system so that the data can be acquired, stored in memory and processed. The various sensors and measuring means are linked to the micro-controller M by conventional electric connections, well known to those skilled in the art.

As a result, it is possible to analyze the signal, for example by measuring the variation in the ultrasonic wave after it has been reflected on an interface, its attenuation and its phase shift, and to calculate from these, by comparison with measurements stored in the memory of the micro-processor M beforehand, the quality of each of the phases and/or the variations in the quality of the fluid phase after separation (these variations being natural to the effluents in the deposit or artificially induced by the means used to activate production), any adjustments being done by analysis at the sampling laboratory in situ, described below with reference to FIG. 3.

The tank 1 comprises, for example, two half-shells, between which the membrane 11 is inserted, extended at its lower section by a pipe.

FIG. 2 shows schematically in greater detail the lower section of the tank and its respective measuring equipment. The transmitter-receiver 21 is positioned, for example, in the lower part of the container so that its transmission-reception axis is substantially vertical and perpendicular to the interfaces existing between the different phases once the effluent has been decanted into the intake chamber. The interfaces detected are, for example, a water/oil interface and an oil/gas interface. A support grid 26 surrounds the transmitter-receiver 21 to prevent the membrane 11 from being perforated (FIG. 1) should any accidental pressure differences occur in the tank 1 when the membrane is at the end of discharging the effluent in the lower part of the tank 1 during the changing of samples, for example.

It is possible to position a grid of a similar structure (not shown in the drawings) in the upper part of the tank 1 close to the pipe 12.

The transmitter-receiver 21 may be encapsulated in a jacket of dielectric material, such as Rilsan, to avoid direct contact with chemically aggressive effluent.

The wall of the tank 1 may have in its lower part seatings or cavities 27, 28 to accommodate respectively the ultrasonic transmitter 22 and receiver 23, the transmitters being positioned opposite each other along an axis and located at a fixed and known distance "L" from each other. They comprise one or several piezo-electric elements, of similar design to the transmitter-receiver 21. The transmission and reception surfaces of these elements open into the pipe 5. The transmitter and receiver are each connected by a coaxial cable 29, for example, inserted in a metal tube 30, to a sealed coaxial electrical connector 51, whose specific role is to provide the electrical connections and transfer of measurements from the device to the micro-controller M and/or to devices located outside the tank and not shown in the drawing. In particular, these devices may be electric tension generators of a type well known to specialists used to operate ultrasonic transmitters and any device needed to operate the apparatus.

The metal tube 30 passes, for example, through the walls of the lower part of the tank by means of sealed, explosion-proof connectors well known to the man skilled in the art, such as the connector glands marketed by the firm, Deutsch, in which the conductors pass through sealed glass pearls. It is made, for example, from sealing material that is mechanically resistant to external pressure and chemical attack from products contained in the effluents, such as $CO_2$, $H_2S$ and brines.

If necessary, piezo-electric ceramics are embedded in a dielectric fluid at equipressure with the static pressure outside the transducer using a metal equipressure blower made from materials that are chemically resistant to petroleum products.

The base may be fitted with an intake pipe 32 opening into an analysis circuit for the effluent, described with reference to FIG. 3.

One of the ways of implementing the method of the invention, for example, is to carry out the following steps: before starting the measuring operations, a position detector 24 is used to ensure that the membrane 11 is in a low position, i.e. located in the lower part of the tank 1. When it has checked this position, the microprocessor M issues a command for the intake chamber 9 to be filled and preferably at the same time for the upper part of the tank located above the membrane 11 to be emptied by commanding the isolating valve 14, valve 20 and valve 6 to open to allow the effluent to pass from the pipe 2 into the tank 1. Simultaneously, it issues a command to the valves 7, 18 and 15 (by-pass) to close. As soon as the detector 25 detects the presence of the membrane 11, it sends a signal to the micro-processor M, indicating that the intake chamber has been completely filled. This signal is an indication to the micro-processor to send a command to close valves 6 and 14 to cut off the tank and simultaneously a command to open the by-pass valve 15.

At the start of filling the intake chamber, the microprocessor records the instant at which the first ultrasonic wave is emitted, which represents a starting top, and records the instant representing the end of the tank filling, coinciding with the command to close the valves 6 and 14. It thereby calculates the total time t needed to fill the tank, which corresponds to the time that has elapsed between these two instants.

After waiting for a certain period of time, for example the time required for the effluent to decant into separate the phases, the micro-processor generates a signal to carry out the various measurements described below. It issues a command to emit an ultrasonic wave from the transmitter 21 at a frequency whose value is selected as being appropriate for the effluent. The propagation direction of the wave is, for example, not parallel to the interface separating the different phases and preferably substantially perpendicular to the interfaces separating the phases that it encounters. The wave may be propagated along a substantially vertical path through the intake chamber. The micro-processor measures the propagation time T1 of this wave on return of the reflection from a first interface separating, for example, the water and the oil, and records this first value. The propagation time measurement is taken by a method well known to specialists, whereby the micro-processor triggers at the moment at which it emits the ultrasonic wave a transmission top and then on return of this wave after reflection from the interface a reception top. The time T1 corresponding to the time elapsed between the transmission top and the reception top represents the double path covered by the wave from the transmitter to the interface and from the interface to the receiver.

In an identical manner, the micro-processor then takes a measurement of a second propagation time T2 coinciding with the reflection of the wave on a second interface, if there is one, such as an oil/gas interface in petroleum effluents, which it then records.

In the case of petroleum effluents containing water, oil and gas, the distribution of the phases after decanting starting from the bottom of the tank is as follows: water-oil-gas.

In this instance, the quantity of the phases may be determined in the following way: using the propagation time T1 and the estimated value of the propagation speed of the wave in the water V1, the micro-processor M determines the height of the water contained in the tank. Knowing the geometric characteristics of the tank, stored in the microcontroller memory beforehand, the processor determines the quantity of water U1. In exactly the same way, it processes the data relating to the second interface and determines the quantity of oil U2 contained in the tank, using the propagation time T2, the estimated value of the propagation speed of a wave in the oil, the geometric characteristics of the tank and the quantity of water U1 determined previously.

The estimated values of the propagation speed of an ultrasonic wave in the water and the oil were obtained, for example, during prior tests carried out previously on substantially monophase phases of a known composition and for given pressure and temperature values, which have then been stored in the microprocessor memory before the tests.

To improve the accuracy of the results, it is possible to determine the real propagation speed of the ultrasonic waves in the phases for the pressure and temperature values prevailing in the tank, these values being measured by appropriate sensors Cp and Ct located in the tank and not shown in the drawing so as to retain clarity.

One way of obtaining the values of the different propagation speeds of an ultrasonic wave is based on the following steps:

after it has been decanted into the tank, the effluent is in the form of several phases, arranged one on top of the other in accordance with density over the height. Thus, the water is located in the lower zone of the tank and partially in the pipe 5 where it is in contact with the transmitter 22 and receiver 23. Using a flight time measurement over the distance "L" separating the transmitter 22 from the receiver 23, the micro-controller M determines the real propagation speed V1 of the wave in the water. To this end, the micro-processor issues a command to the transmitter 22 to emit a wave and a reception command to the receiver 23.

the micro-controller then issues a command signal to open the outlet valve 7, the valves 18 and 14 and to close the by-pass valve 15 until the oil reaches the transmitter 22. This operation, known as draining, is controlled, for example, in the following way: the propagation time T2 of the wave in the oil is already known from previous measurements and, using the estimated speed value, the micro-processor is able to determine the height of the oil Hh in the tank, which corresponds to (T2–T1)/V2 and hence, by combining the geometric characteristics of the tank, the quantity of oil Uh. Since it knows the time taken to completely fill the tank t, the quantity of water Ue, the quantity of oil Uh and the average flow rate Qt (given by the ratio of the volume of the tank to the time taken to completely fill the tank), the micro-controller determines the time Tp=(Ue+Uh)/Qt needed to evacuate the water and, for example, at least half of the oil. The tank is drained over a period of time Tp so that the oil is in contact with the transmitter 22 and receiver 23. The micro-controller then determines, by proceeding with the steps described above, the real speed V2 at which an ultrasonic wave is propagated in an organic phase such as oil. Using the real propagation speeds V1 and V2 of an ultrasonic wave in the water and in the oil and the time measurements T1 and T2, the micro-processor determines accurately the respective quantities Ue and Uh of water and oil contained in the tank.

The quantity of gas Ug is calculated using, for example, the quantities of water Ue, oil Uh and the total volume of the tank Ur.

As the time t taken to completely fill the tank is known as well as the respective quantities of water, oil and gas, the micro-processor is able to calculate from these the respective values of the flow rates Qe of the water, Qh of the oil and Qg of the gas and the usual ratios known as GOR (Gas Oil Ratio) and GLR (Gas Liquid Ratio) at the pressure and temperature levels of the tank, these latter two values being measured by specially adapted pressure and temperature sensors, not shown in the drawings.

Advantageously, the improved control of draining the container can be obtained by using as an outlet valve a control valve with a variable section, such as an adjustable choke.

Advantageously, this adjustable choke restricts the speed at which the interfaces separating the phases of an effluent descend so as to prevent disturbance such as waves and the vortex phenomenon in the container and thus keep the interfaces substantially horizontal.

By correlating the repeated flight time measurements and the variations in the amplitude of the signals or echoes of the wave reflected by the interface, it is possible to ascertain the position of these interfaces at any time whilst the container is being emptied.

The position of the first oil/water interface may be detected and controlled, for example, using a variation in the flight time, such as its decrease, and the amplitude of the first reflected signal or first echo.

The position of the second oil/gas interface may be controlled in exactly the same way using the values of the second reflected signal or echo.

The measurement of the flight time correlated with a value of the wave speed in the oil, pre-recorded in the micro-controller, enables the position of a level in the container to be determined and, at a given value, the drain valve to be closed. The second effluent phase, for example the oil, is thus in the lower volume section of the container, in the zone in which the sensors measuring the real propagation speed of the waves in the effluent are located.

The drain valve remains in the closed position over a sufficient period of time for this real propagation speed in the second effluent to be measured.

The values of the propagation speeds measured in the two main liquid effluents are entered in the memory of the micro-processor. These enable the flow rates for each phase to be obtained, for example. It is not necessary in the case of a given effluent deposit or well under production to check the propagation speeds systematically at each filling/emptying of the container. However, it is useful to check the possible variations so as to ensure smooth operation of the measuring apparatus and follow in time any changes in the properties of the effluents, particularly where treated fluids are being injected into surrounding wells.

Another way of proceeding is to carry out a quality check on the phase for which real speed is being measured. This may be done in the following way: the signal received by the receiver 23 is analyzed in terms of amplitude and/or phase and compared with values previously stored in the microprocessor M.

Hence, at a given temperature and pressure, the absorption values of an ultrasonic wave expressed in dB/cm are, for example:

for a refined oil or a light crude, equal to 0.13, for a thick crude equal to 0.91, for a sea water equal to 0.007, and 0.06 for a vary saline deposit water, for the gas, the attenuation is very high and depends on whether its constitution is complex, its pressure, its temperature and its frequency.

The difference between these values is nevertheless sufficient to differentiate these three phases when a wave of the same given transmission power and frequency is used. This may be confirmed by using the frequency staggering technique, known to those skilled in the art and not described here. Particularly in the case of gas, it is desirable to use frequencies close to the audible frequencies.

Preferably, measurements are taken continuously, allowing the microprocessor to relate the nature of a phase to a flight time measurement.

The method as described above has the advantage of providing a device which will automatically clean the container and thus improve the useful life of the membrane.

After carrying out a series of measurements in the manner described above with reference to FIGS. 1 and 2, for example, this is done by the following stages. Once the measuring cycle has been completed, an operation is commenced whereby the fluid sample on which measurements have just been taken is discharged. The micro-processor issues a signal to command the opening of the by-pass valve 18, the isolating valve 14 and the outlet valve 7 and simultaneously orders valve 6 and valve 15 into the closed position. The fluid drawn from pipe 2 then passes through into the decanting flask D, where its speed is slowed down, followed by the filter F located in the upper part of the flask, the valve 20 being in a closed position. This filter is, for example, a filter calibrated to one hundred microns of the type conventionally used by a specialist, particularly in the petroleum industry. The fluid then passes through the upper pan of the container via the pipe 12 above the membrane and pushes the membrane back towards the lower part of the container. When the sensor 24 detects that the membrane 11 has reached the position in the lower part of the container, it issues a signal to the micro-processor indicating that discharge of sample fluid has been completed, representing an end of one measuring cycle. Another measuring cycle may then be activated.

Throughout all the phases, filling, measuring and discharge of the intake chamber 9, the transmitter-receiver 21, the transmitter-receiver 22 and the receiver 23 are kept in operating mode, which prevents any particles from forming sediment and sticking to the transmission surface which is therefore self-cleaning, the cleaning frequency varying with the measuring frequency.

The particles placed in suspension by the transmitter 21 as a result of the mechanical effect induced by the ultrasonic wave, are discharged via the filling holes 26 which may be substantially identical in nature to the nature of the filter F of the decanter, so as to suit the size of the grains of sand carried by the liquid effluents. Discharge of the sample again cleans the filter grid by circulating the effluent in reverse.

Reducing the speed of the fluid encourages any solid particles in the fluid to be deposited in the lower part of the decanting flask D. Fluid is introduced preferably through a lateral inlet of the decanter flask D, off-centre, thus generating a cyclone effect that will be conducive to separating the solid particles from the effluent.

The filter F is cleaned during the phase when the intake chamber is being filled with the fluid sample to be analyzed. In effect, during this filling stage, the fluid sample pushes the membrane back towards the upper part of the container and thus causes the fluid contained between the membrane and the upper part of the container to be discharged through the pipe 12. The discharged fluid passes into the decanting flask in a direction opposite to that in which it was introduced and chases any solid particles that might have been deposited on the lower surface of the membrane away. This prevents any obstruction of the filter.

During this operation, the valve 19 is open and allows fluid to pass through into the discharge pipe 3. Any solid particles that have been deposited on the lower part of the regulator flask are carried away (these particles may have built up during the phase when the decanter flask and/or filter was/were being filled).

This procedure has the advantage of operating as a self-cleaning system which protects the upper surface of the membrane against trapped particles, such as sand particles.

In another embodiment described in relation to FIG. 3, the device offers the possibility of carrying out an on-line control of the composition of the effluent.

Operation of such a system is facilitated if the intake 31 and return 32 pipes are positioned closed to the transmitters and receivers situated in the pipe 5. In effect, during the operation, which consists in draining the intake chamber, the different phases of water, oil and gas have to pass in front of the measuring elements.

The intake 31 and return 32 pipes are linked to an intake circuit P supplying a series of analyzers arranged in a sealed housing 34 and pressured to atmospheric pressure.

The intake circuit comprises a remotely controlled valve 35 and a branch 36 normally closed off by the valve 37, which is fed with sea water to rinse out the circuits. The decanted water from the effluents may also be used.

The container 34 protecting the series of analyzers comprises various elements allowing the fluid to be analyzed, such as heating means 38, a thermal conductivity analyzer 39, a viscosity analyzer with coaxial cylinders, a pressure and temperature controller 40, a vibrating densitometer 41, a pH-meter 42, a resistivity analyzer 43 and a circulation pump 44 for the samples.

After analysing the fluid samples, the samples return to the intake chamber via the pipe 33 which may be closed off by a valve 45 and the pipe 32. The return circuit comprises a by-pass branch and a valve 46 which in particular allows the rinsing water to be returned to the sea or a sample taken from the sea water used for the control and the recalibration of the measuring apparatus described above.

The valves located on the pipes are preferably remotely controlled.

The effluent sample taken can be checked to ensure that it is representative by using a control device such as that described in French patent FR 2.633.719 by the applicant or any other device capable of carrying out such a control.

The results provide a measuring accuracy to less than one percentage point, which means that a device may be used, for example, such as a calibrating device specifically for controlling continuously running apparatus, installed on oil fields under production or testing stations. This equipment may therefore be regulated or checked at any time irrespective of the type of multiphase flow, whether it has bubbles, is stratified, has waves or plugs.

The methods used to measure propagation times, the outward and return and absorption of the ultrasonic waves used to implement the present invention and their processing are well known. They are based on the methods used in sub-marine detection sonars or seismic analysis techniques used on sedimentary layers well known to those skilled in the field of geology. By preference, the methods used in the medical field and more especially the methods used to carry out ultrasonic echographs will be used.

Tests carried out on different fluids, whose characteristics are analyzed in the table below and obtained at a frequency value of 1 MHz, produced good results in detecting the different interfaces.

These values are given for a temperature ranging between 0° and 20° C., at which the acoustic impedance values are substantially stable. The effect of the pressure value on the respective operating range is negligible.

| Fluid | Acoustic impedance given in Rayls | Value of impedance ratios | Phase |
|---|---|---|---|
| Fresh water | $1.43\ 10^6$ | | Phase 1, |
| Sea water | $1.55\ 10^6$ | | for example |
| Deposit water | $2.2\ 10^6$ | | |
| | | water/oil 1.1–2 | |
| Refined oil | $1.2\ 10^6$ | | Phase 2 |
| Crude 1 | $1.1\ 10^6$ | | |
| Crude 2 | $1.3\ 10^6$ | | |
| | | $1.5 10^3$ $\rightarrow 4 10^3$ | |
| Methane | 308 | oil/gas | Phase 3 |
| Carbon dioxide | 662 | | |
| Air | 428 | | |

Crudes 1 and 2 are from effluents after the aqueous phase and the gaseous phase have been separated. They may be likened to the organic phase in terms of acoustic impedance values, for example.

In order to eliminate variations in the values of acoustic impedances caused by temperature, it is possible to insulate the tank.

Clearly, various modifications and/or additions may be made by the man skilled in the art to the method and device described above for the purposes of illustration and not limitative, without departing from the scope of the invention.

I claim:

1. A device for determining the composition of a mulitphase fluid made of several phases, the phases being separated by an interface, at least two of the phases having acoustic impedances of essentially remote values and at least two of the phases having acoustic impedance values essentially close but different, said fluid possibly containing solid particles, comprising a container linked to at least one intake pipe for said multiphase fluid, at least one means located in the container for generating a first ultrasonic wave in a direction not parallel to an interface separating at least two phases, said first means being designed to receive at least one signal from the reflection of the first ultrasonic wave when the first ultrasonic wave encounters an interface separating two phases, second means for emitting and receiving a second ultrasonic wave and processing means, characterized in that the second means are arranged so as to transmit and receive the second ultrasonic wave in a direction substantially perpendicular to the direction of propagation of the first ultrasonic wave, and in that said processing means enable the propagation time of the second wave through a phase to be measured and based on data stored in the processing means together with the propagation time measurements, enables the quantity of at least one of the phases contained in the multiphase fluid to be determined, and a filter system to prevent any build-up of particles in the lower part of the container.

2. A device for determining the composition of a mulitphase fluid made of several phases, the phases being separated by an interface, at least two of the phases having acoustic impedances of essentially remote values and at least two of the phases having acoustic impedance values essentially close but different, said fluid possibly containing solid particles, comprising a container linked to at least one intake pipe for said multiphase fluid, at least one means located in the container for generating a first ultrasonic wave in a direction not parallel to an interface separating at least two phases, said first means being designed to receive at least one signal from the reflection of the first ultrasonic wave when the first ultrasonic wave encounters an interface separating two phases, second means for emitting and receiving a second ultrasonic wave and processing means, characterized in that the second means are arranged so as to transmit and receive the second ultrasonic wave in a direction substantially perpendicular to the direction of propagation of the first ultrasonic wave, and in that said processing means enables the propagation time of the second wave through a phase to be measured and based on data stored in the processing means together with the propagation time measurements, enables the quantity of at least one of the phases contained in the multiphase fluid to be determined, and means for driving and controlling a means for filling and emptying the container.

3. A method of determining by means of at least one ultrasonic wave the composition of a multiphase fluid having several phases, at least a first and a second phase having essentially remote acoustic impedance values and at least the second phase and a third phase having acoustic impedance values substantially close but different, said fluid possibly containing solid particles, characterized in that:

a) at least a proportion of the multiphase fluid is drawn off into a container for analysis.

b) the multiphase fluid is left to decant over a sufficient period of time to allow the various phases to separate, c) a first ultrasonic wave is emitted in a direction not parallel to a first interface separating two phases, the wave is propagated and passes through the container, d) by means of an appropriate device, at least a first propagation time T1 is measured representing the reflection of said first ultrasonic wave on a first interface, e) a second ultrasonic wave is emitted, in a direction substantially perpendicular to the direction of propagation of the first ultrasonic wave, through a first phase when this first phase is located in the lower section of the container and the propagation time T'1 of the second wave in this first phase is measured in order to calculate the real propagation speed V1 of the wave in the first phase, f) at least the propagation time T1 and a propagation time T2 are measured representing respectively the reflection of the first ultrasonic wave on the first and second interface separating respectively the first and second phases and the second and third phases, g) the real propagation speed of the wave in the first phase is measured in accordance with step e), h) the fluid is drained from the container over a sufficient period of time to allow the second phase to reach the level of the lower section of the container, another second ultrasonic wave is sent in a direction substantially perpendicular to the propagation direction of the first wave, through the second phase, this phase being located in the lower section of the container, and the propagation time T'2 of the second wave in this second phase is measured in order to determine the real propagation speed V2 of the wave in the second phase, and i) using the propagation time T1 and T2, the values of real speeds V1 and V2 and the geometric characteristics of the container, the quantities U1 and U2 of the first and second phases are determined.

4. A method as claimed in claim 3, characterized in that in the case of a multiphase fluid comprising at least three phases, the quantity of the third phase is determined using the geometric characteristics of the container and the quantities U1 and U2.

5. A method as claimed in claim 3 for detecting a first interface located between an aqueous phase and an organic phase and a second interface between an organic phase and a gaseous phase, these phases making up the greater part of petroleum effluent.

6. A method as claimed in claim 3 for determining the flow rate of each of the phases contained in a petroleum effluent.

7. A method of determining by means of at least one ultrasonic wave the composition of a multiphase fluid having several phases, at least two of these phases having acoustic impedance of different values, this fluid possibly containing solid particles, characterized in that:

a) at least a portion of the multiphase fluid is drawn off into a container for analysis, b) the multiphase fluid is left to decant over a sufficient period of time to allow the various phases to separate, c) a first ultrasonic wave is emitted in a direction not parallel to a first interface separating two phases, the wave is propagated and passes through the container, d) by means of an appropriate device, at least a first propagation time T1 is measured representing the reflection of this first ultrasonic wave on a first interface, e) a second ultrasonic wave is emitted, in a direction substantially perpendicular to the direction of propagation of the first wave, through a first phase when this first phase is located in the lower section of the container and the propagation time T'1 of the second wave in this first phase is measured in order to calculate the real propagation speed V1 of the wave in the first phase, and f) using the first propagation time T1, the value of the real speed V1 and the geometric characteristics of the container, the quantity U1 of the first phase in the container is determined; the attenuation of the first wave being measured after the first wave has reflected on the first interface.

8. A method of determining by means of at least one ultrasonic wave the composition of a multiphase fluid having several phases, at least two of these phases having acoustic impedance of different values, this fluid possibly containing solid particles, characterized in that:

a) at least a portion of the multiphase fluid is drawn off into a container for analysis, b) the multiphase fluid is left to decant over a sufficient period of time to allow the various phases to separate, c) a first ultrasonic wave is emitted in a direction not parallel to a first interface separating two phases, the wave is propagated and passes through the container, d) by means of an appropriate device, at least a first propagation time T1 is measured representing the reflection of this first ultrasonic wave on a first interface, e) a second ultrasonic wave is emitted, in a direction substantially perpendicular to the direction of propagation of the first wave, through a first phase when this first phase is located in the lower section of the container and the propagation time T'1 of the second wave in this first phase is measured in order to calculate the real propagation speed V1 of the wave in the first phase, and f) using the first propagation time T1, the value of the real speed V1 and the geometric characteristics of the container, the quantity U1 of the first phase in the container is determined, and further characterized in that the method enables the accumulation of deposits of solid particles in the container fitted with a membrane to be avoided by carrying out the following steps:

at least a proportion of the multiphase fluid, referred to as the analysis sample, is drawn off into the container, the proportion of fluid drawn off is left to decant and measurements are taken in accordance with steps a) to f), when the measurements have been completed, a quantity of fluid which has been passed beforehand through a filtering device is introduced through the upper part of the container, the quantity of fluid being sufficient to push a membrane towards the lower part of the container so as to discharge the multiphase fluid sample, any particles that have formed a sendiment in the lower part of the container being carried with the sample discharged from the container.

9. A method of determining by means of at least one ultrasonic wave the composition of a multiphase fluid having several phases, at least two of these phases having acoustic impedance of different values, this fluid possibly containing solid particles, characterized in that:

a) at least a portion of the multiphase fluid is drawn off into a container for analysis, b) the multiphase fluid is left to decant over a sufficient period of time to allow the various phases to separate, c) a first ultrasonic wave is emitted in a direction not parallel to a first interface separating two phases, the wave is propagated and passes through the container, d) by means of an appropriate device, at least a first propagation time T1 is measured representing the reflection of this first ultrasonic wave on a first interface, e) a second ultrasonic wave is emitted, in a direction substantially perpendicular to the direction of propagation of the first wave, through a first phase when this first phase is located in the lower section of the container and the propagation time T'1 of the second wave in this first phase is measured in order to calculate the real propagation speed V1 of the wave in the first phase, and f) using the first propagation time T1, the value of the real speed V1 and the geometric characteristics of the container, the quantity U1 of the first phase in the container is determined, and further characterized in that the time t required to completely fill the container is measured and the flow rate of each of the phases making up said fluid is calculated on the basis of this time t.

10. A method of determining by means of at least one ultrasonic wave the composition of a multiphase fluid having several phases, at least two of these phases having acoustic impedance of different values, this fluid possibly containing solid particles, characterized in that:

a) at least a portion of the multiphase fluid is drawn off into a container for analysis, b) the multiphase fluid is left to decant over a sufficient period of time to allow the various phases to separate, c) a first ultrasonic wave is emitted in a direction not parallel to a first interface separating two phases, the wave is propagated and passes through the container, d) by means of an appropriate device, at least a first propagation time T1 is measured representing the reflection of this first ultrasonic wave on a first interface, e) a second ultrasonic wave is emitted, in a direction substantially perpendicular to the direction of propagation of the first wave, through a first phase when this first phase is located in the lower section of the container and the propagation time T'1 of the second wave in this first phase is measured in order to calculate the real propagation speed V1 of the wave in the first phase, and f) using the first propagation time T1, the value of the real speed V1 and the geometric characteristics of the container, the quantity U1 of the first phase in the container is determined, and further characterized in that a check is carried out as to whether the multiphase fluid drawn off while filling the container is representative.

* * * * *